(12) United States Patent
Alkhatib et al.

(10) Patent No.: US 11,590,708 B2
(45) Date of Patent: *Feb. 28, 2023

(54) THREE-DIMENSIONAL FLUID MICROMODELS

(71) Applicant: Saudi Arabian Oil Company, Dhahran (SA)

(72) Inventors: Ali Alkhatib, Dhahran (SA); Amar Alshehri, Dhahran (SA); Ming Han, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 1288 days.

This patent is subject to a terminal disclaimer.

(21) Appl. No.: 16/014,525

(22) Filed: Jun. 21, 2018

(65) Prior Publication Data

US 2018/0300947 A1    Oct. 18, 2018

Related U.S. Application Data

(62) Division of application No. 14/700,408, filed on Apr. 30, 2015, now Pat. No. 10,055,884.

(51) Int. Cl.
  *B29C 64/386*   (2017.01)
  *G06T 17/00*    (2006.01)
  (Continued)

(52) U.S. Cl.
  CPC ............ *B29C 64/386* (2017.08); *B29C 64/20* (2017.08); *G01N 33/24* (2013.01); *G06T 17/00* (2013.01);
  (Continued)

(58) Field of Classification Search
  CPC ...... B29C 64/386; B29C 64/20; G01N 33/24; G06T 17/00
  (Continued)

(56) References Cited

U.S. PATENT DOCUMENTS 7,254,091 B1  8/2007  Gunning
8,260,589 B1  9/2012  Kumar
(Continued)

FOREIGN PATENT DOCUMENTS

CN      103806905        5/2014
WO    WO2014/003596      1/2014

OTHER PUBLICATIONS

Gulf Cooperation Council Examination Report issued in GCC Application No. GC 2016-31040 dated Sep. 26, 2018, 3 pages.
(Continued)

*Primary Examiner* — Ahshik Kim
(74) *Attorney, Agent, or Firm* — Fish & Richardson P.C.

(57) ABSTRACT

The subject matter of this specification can be embodied in, among other things, a system that includes a three-dimensional fabricator. An image processing module acquires an image of a rock sample having a network of pores, a transformation module transforms the image into a binary matrix and determine a set of statistical moments of the binary matrix, a layer generation module generates a first representation of a first stochastic layer based on the set and emulative of the rock sample and generates a second representation of a second stochastic layer based on the set and emulative of the rock sample. An arrangement module arranges the first representation and the second representation as adjacent layers of a three-dimensional model emulative of the rock sample, and provides the first representation and the second representation to the 3D fabricator for fabrication as a physical three-dimensional fluid micromodel emulative of the rock sample.

10 Claims, 7 Drawing Sheets

(51) Int. Cl.
*G01N 33/24* (2006.01)
*B29C 64/20* (2017.01)
*B33Y 10/00* (2015.01)
*B33Y 50/00* (2015.01)
*G01V 99/00* (2009.01)

(52) U.S. Cl.
CPC .............. *B33Y 10/00* (2014.12); *B33Y 50/00* (2014.12); *G01V 99/00* (2013.01); *G06T 2200/04* (2013.01); *G06T 2200/08* (2013.01)

(58) Field of Classification Search
USPC ........................................................ 700/117
See application file for complete search history.

(56) References Cited

U.S. PATENT DOCUMENTS

| | | | |
|---|---|---|---|
| 2009/0259446 | A1 | 10/2009 | Zhang |
| 2011/0004447 | A1 | 1/2011 | Hurley et al. |
| 2012/0221306 | A1 | 8/2012 | Hurley et al. |
| 2012/0281883 | A1 | 11/2012 | Hurley et al. |
| 2013/0180327 | A1 | 7/2013 | Frederick |
| 2013/0235412 | A1 | 9/2013 | Baldwin |
| 2014/0076544 | A1 | 3/2014 | Lecerf et al. |
| 2017/0132781 | A1* | 5/2017 | Roth ................... G01N 33/241 |
| 2018/0120215 | A1* | 5/2018 | Jin ...................... G01N 15/08 |
| 2022/0156901 | A1* | 5/2022 | Song ................... G01N 33/241 |

OTHER PUBLICATIONS

European Patent Office Communication Pursuant to Article 94(3) in European Application No. 15802222.8 dated Aug. 8, 2018, 4 pages.
Alshehri et al., "Pore-Level Mechanics of Forced and Spontaneous Imbibition of Aqueous Surfactant Solutions in Fractured Porous Media", SPE 124946, Copyright 2009, 17 pages.
Bou-Mikael, "Design and Optimization of 2.5 Dimension Porous Media Micromodel for Nanosensor Flow Experiments," May 2012, 84 pages.
Buchgraber et al., "The Displacement of Viscous Oil by Associative Polymer Solutions," SPE 122400, Copyright 2009, 19 pages.
Hajizadeh et al., "An Algorithm for 3D Pore Space Reconstruction from a 2D Image Using Sequential Simulation and Gradual Deformation with the Probability Perturbation Sampler," Transport in Porous Media, Kluwer Acedemic Publishers, Do., vol. 94, No. 3, Jun. 20, 2012, 23 pages.
Haralick et al., "Computer Classification of Reservoir Sandstones," Sep. 11, 1972, pp. 171-177.
Hasiuk, "Making Things Geological: 3-D Printing in the Geosciences," GSA Today, vol. 24, No. 8, Aug. 2014, pp. 28-29.
Hornbrook, "Visualization of Foam/Oil Interactions in a New, High Resolution Sandston Replica Micromodel," Sep. 1991, 48 pages.
Inwood, "High-Resolution, Microvisual Study of High Mobility Ratio, Immiscible Displacements," Jun. 2008, 104 pages.
Ishutov et al., "3-D Printing Artificial Reservoir Rocks to Test their Petrophysical Properties," Search and Discovery Article #41427, Aug. 29, 2014, 18 pages.
Jaber, "Low Tension Methods for Fractured Resources," Jun. 2009, 82 pages.
Rangel-German et al., "A Micromodel Investigation of Two-Phase Matrix-Fracture Transfer Mechanisms," Water Resources Research, vol. 42, Mar. 7, 2006, 13 pages.
Tsang et al., "Flow Channeling in a Single Fracture as a Two-Dimensional Strongly Heterogeneous Permeable Medium," Water Resources Research, vol. 25, No. 9, Sep. 1989, pp. 2076-2080.
Wang et al., "The Study of Porous Media Reconstruction using a 2D Micro-CT Image and MPS," Computational Intelligence and Software Engineering, Dec. 11, 2009, 5 pages.
Smith "Hot New Additive Manufacturing Materials" in Protype / Manufacture dated Nov. 1, 2011; retrieved from http://www.digitaleng.news/de/hot-new-additive-manufacturing-materials (Year: 2011).
Brown et al. "Experimental observation of fluid flow channels in a single fracture"; Journal of Geophysical Research, vol. 103, No. B3, pp. 5125-5132, Mar. 10, 1998 (Year: 1998).
PCT International Search Report and Written Opinion of the International Searching Authority, PCT/US2015/057483, dated Jan. 21, 2016, 13 pages.
European Patent Office Communication Article 67(3) EPC in European Application No. 15802222.8 dated Feb. 7, 2018, 1 page.
Communication Pursuant to Article 94(3) EPC issued in European Application No. 15802222.8 dated Dec. 19, 2018, 4 pages.
Communication Pursuant to Article 94(3) EPC issued in European Application No. 15802222.8 dated May 16, 2019, 4 pages.
CN Office Action in Chinese Appln. No. 201580081205, dated Aug. 9, 2019, 23 pages (with English translation).
Gulf Cooperation Council Examination Report issued in GCC Application No. GC 2016-36772 dated Sep. 8, 2019, 4 pages.
Gulf Cooperation Council Examination Report issued in GCC Application No. GC 2016-36772 dated Dec. 30, 2019, 3 pages.

* cited by examiner

THREE-DIMENSIONAL FLUID MICROMODELS

CROSS-REFERENCE TO RELATED APPLICATIONS

This application is a divisional application of and claims the benefit of priority to U.S. application Ser. No. 14/700,408, filed on Apr. 30, 2015, the contents of which are hereby incorporated by reference.

TECHNICAL FIELD

This instant specification relates to the fabrication of fluid micromodels.

BACKGROUND

Multiphase flow of miscible fluids in porous media is determined by pore-scale processes. Pore-level observations of fluid flow as well as oil and gas-trapping mechanisms can be used as tools for estimating the behaviors of fluids in porous media at larger scale. Such observations can also provide validation of pore network models and direct numerical simulations of fluid flow.

To produce micromodels, etching of glass or silicon wafers using photolithographic techniques is commonly used. With these methods, an essentially two-dimensional pore network is etched with a certain uniform thickness with little to no connectivity in the third dimension. As such, current micromodels do not fully capture connectivity of reservoir rocks since such rocks exhibit connectivity in three dimensions rather than two dimensions.

SUMMARY

In general, this document describes the fabrication of three-dimensional fluid micromodels.

In a first aspect, a method includes acquiring, by a computer device, an image of a section of a rock sample having a network of pores, transforming, by the computer device, the image into a binary matrix, generating, by the computer device, a first representation of a first stochastic layer based on a set of one or more statistical moments of the binary matrix and emulative of the rock sample, generating, by the computer device, a second representation of a second stochastic layer based on the set and emulative of the rock sample, the second representation being different from the first representation, arranging, by the computer device, the first representation and the second representation such that the first stochastic layer and the second stochastic layer are arranged as adjacent layers of a three-dimensional model emulative of the rock sample, and providing, by the computer device, the arrangement of the first representation and the second representation as adjacent layers of the three-dimensional model emulative of the rock sample.

Various implementations can include some, all, or none of the following features. Arranging the first representation and the second representation can further include forming, under control of the computer device, the three-dimensional model emulative of the rock sample as a physical three-dimensional fluid micromodel emulative of the rock sample, and the forming can include forming a first physical micromodel layer comprising a network of pores based on the first representation, and forming a second physical micromodel layer comprising a network of pores based on the second representation adjacent the first physical micromodel layer. Forming a physical three-dimensional fluid micromodel emulative of the rock sample can include forming using a three-dimensional printer. Forming the first physical micromodel layer can also include providing, by the computer device, the first representation as a first collection of commands to the three-dimensional printer, and printing, by the three dimensional printer, the first physical micromodel layer as a first printed layer in a physical three-dimensional printed model, and forming at least the second physical micromodel layer can also include providing, by the computer device, the second representation as a second collection of commands to the three-dimensional printer, and printing, by the three dimensional printer, the second physical micromodel layer as a second printed layer in the physical three-dimensional printed model. Arranging the first representation and the second representation can also include arranging, by the computer device, the first representation and the second representation into a computer-generated three-dimensional representation based on the set, the computer generated three-dimensional representation comprising a computer generated three-dimensional network of pores emulative of the rock sample. The method can also include identifying, by the computer device, at least one outer boundary of the computer generated three-dimensional representation, and removing pores from the outer boundary. The method can also include including in the computer generated three-dimensional representation at least one of an injection port or a production port. The method can also include transforming a degree of heterogeneity of the computer generated three-dimensional representation by applying a moving average to the distribution of the three-dimensional network of pores within the computer generated three-dimensional representation. The method can also include determining, by the computer device, the set of one or more statistical moments of the binary matrix. The set can include one or more of a statistical mean and a statistical covariance.

In a second aspect, a non-transitory computer-readable medium stores instructions executable by a processing device to perform operations including acquiring, by a computer device, an image of a section of a rock sample having a network of pores, transforming, by the computer device, the image into a binary matrix, generating, by the computer device, a first representation of a first stochastic layer based on a set of one or more statistical moments of the binary matrix and emulative of the rock sample, generating, by the computer device, a second representation of a second stochastic layer based on the set and emulative of the rock sample, the second representation being different from the first representation, arranging, by the computer device, the first representation and the second representation such that the first stochastic layer and the second stochastic layer are arranged as adjacent layers of a three-dimensional model emulative of the rock sample, and providing, by the computer device, the first representation and the second representation as adjacent layers of the three-dimensional model emulative of the rock sample.

Various implementations can include some, all, or none of the following features. Arranging the first representation and the second representation can include forming, under control of the computer device, the three-dimensional model as a physical three-dimensional fluid micromodel emulative of the rock sample, and the forming can include forming a first physical micromodel layer comprising a network of pores based on the first representation, and forming a second physical micromodel layer comprising a network of pores based on the second representation adjacent the first physical micromodel layer. Forming the three-dimensional model as the physical three-dimensional fluid micromodel emulative of the rock sample can include providing, by the computer device, the first representation as a first collection of commands to a three-dimensional printer, and printing, by the three dimensional printer, the first physical micromodel layer as a first printed layer in a physical three-dimensional printed model, and forming at least the second physical micromodel layer can also include providing, by the computer device, the second representation as a second collection of commands to the three-dimensional printer, and printing, by the three dimensional printer, the second physical micromodel layer as a second printed layer in the physical three-dimensional printed model. Arranging the first representation and the second representation can also include arranging, by the computer device, the first representation and the second representation into a computer-generated three-dimensional representation based on the set, the computer-generated three-dimensional representation comprising a three-dimensional network of pores emulative of the rock sample, and transforming, by the computer device, a degree of heterogeneity of the computer-generated three-dimensional representation by applying a moving average to the distribution of the three-dimensional network of pores within the computer-generated three-dimensional representation. The operations can also include identifying, by the computer device, at least one outer boundary of the computer-generated three-dimensional representation, and removing pores from the outer boundary. The operations can also include determining, by the computer device, the set of one or more statistical moments of the binary matrix, wherein the set comprises one or more of a statistical mean and a statistical covariance.

In a third aspect, a system includes a three-dimensional fabricator, an image processing module configured to acquire an image of a section of a rock sample having a network of pores, a transformation module configured to transform the image into a binary matrix and determine a set of one or more statistical moments of the binary matrix, the set comprising one or more of a statistical mean and a statistical covariance, a layer generation module configured to generate a first representation of a first stochastic layer based on the set and emulative of the rock sample and generate a second representation of a second stochastic layer based on the set and emulative of the rock sample, the second representation being different from the first representation, and an arrangement module configured to arrange the first representation and the second representation such that the first stochastic layer and the second stochastic layer are arranged as adjacent layers of a three-dimensional model emulative of the rock sample and provide the first representation and the second representation to the 3D fabricator for fabrication as a physical three-dimensional fluid micromodel emulative of the rock sample. The physical three-dimensional fluid micromodel includes a first physical micromodel layer comprising a network of pores based on the first representation, and a second physical micromodel layer comprising a network of pores based on the second representation, adjacent the first physical micromodel layer.

Various embodiments can include some, all, or none of the following features. The arrangement module can be a three-dimensional printer, the first representation can be presented as a first collection of commands to the three-dimensional printer for printing as a first printed layer in the physical three-dimensional fluid micromodel, and the second representation can be presented as a second collection of commands to the three-dimensional printer for printing as a second printed layer in the physical three-dimensional fluid micromodel. The arrangement module can be further configured to arrange the first representation and the second representation into a computer-generated three-dimensional representation based on the set, the computer-generated three-dimensional representation comprising a three-dimensional network of pores emulative of the rock sample, and identify at least one outer boundary of the three-dimensional computer-generated representation, and remove pores from the outer boundary. The arrangement module can be further configured to arrange the first representation and the second representation into a three-dimensional representation based on the set, the three-dimensional representation comprising a three-dimensional network of pores emulative of the rock sample, and transform a degree of heterogeneity of the three-dimensional representation by applying a moving average to the distribution of the three-dimensional network of pores within the three-dimensional representation.

The details of one or more implementations are set forth in the accompanying drawings and the description below. Other features and advantages will be apparent from the description and drawings, and from the claims.

DETAILED DESCRIPTION

This specification describes systems and techniques for the fabrication of fluid micromodels that emulate porous media (e.g., such as oil and/or gas trapping underground rock) having pore connectivity in three dimensions. In general, a slice of porous rock is imaged and processed to determine a mathematical model that describes the sizes and distributions of rock and pores in the sample. The mathematical model is then used to create multiple two-dimensional arrays as computer models of layers that emulate thin sections of the rock sample. Multiple such two-dimensional arrays are stacked to generate a three-dimensional computer model. In each two-dimensional array, the binary values are stochastically varied. Such stochastic variation randomly distributes the porosity and non-porosity across the three-dimensional computer model resulting in the three-dimensional computer model having an interconnectivity that approximates the interconnectivity of reservoir rock. A three-dimensional (3D) fabricator, such as a 3D printer, is used to produce physical embodiments of these models, forming one layer on top of another to create a physical model having 3D pore connectivity that is emulative of the original rock sample. Transparent materials are used in the formation of the physical model to allow for direct visualization of fluid-flow experiments within the produced 3D network.

The systems and techniques described here may provide one or more of the following advantages. First, the systems can provide a full characterization of a pore network. Second, the systems can provide reproducible pore network models. Third, the systems can provide pore network models having a vertical variation that is representative of reality, a feature unavailable in substantially two-dimensional micromodels. Fourth, the systems can provide pore network models having a physical manifestation of uncertainty in heterogeneity, which can enhance understanding of the effect of uncertainty on fluid flow experiments. Fifth, the systems can provide control over fluid and rock interactions because the properties of rock to be simulated are known, and a 3D model can be made from a material that has properties of that rock.

Figure 1:
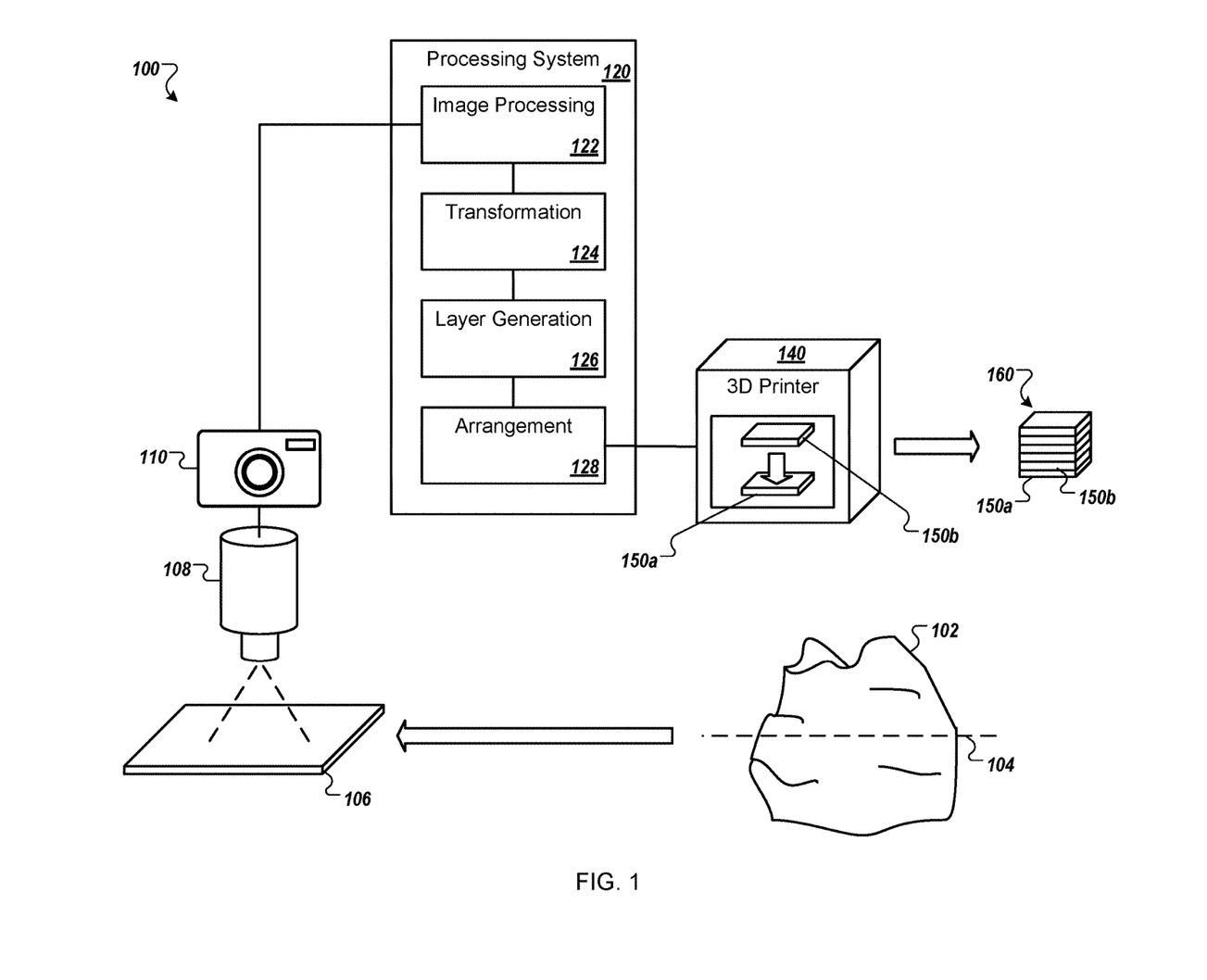
FIG. 1 is a schematic diagram that shows an example of a system for fabrication of fluid micromodels.

FIG. 1 is a schematic diagram that shows an example of a system 100 for fabrication of 3D fluid micromodels. A sample 102 of porous rock or other porous material is obtained (e.g., a core sample of a gas or oil bearing underground porous rock formation such as Berea sandstone). The sample 102 is sliced, as represented by the line 104, to obtain a slice 106. Preparation of thin sections results, visually, in the reduction of the 3D flow space of the sample 102 to a two-dimensional approximation. In some implementations, creation of the slice 106 can cause some continuous pores to be made discontinuous while some new, continuous flow paths may be created. In some embodiments, the sample 102 may be filled with an epoxy to fill substantially all the void spaces within the sample 102 (e.g., to stabilize the structure of the pore network before slicing).

The slice 106 is magnified under a microscope 108 to reveal details of the sizes, locations, and distributions of rock and pores across the slice 106. In some implementations, the pore configuration of the sample 102 can be determined before the creation of a thin section by changing the focal length of the microscope. For example, microscopic analysis can be used on the Berea sandstone sample section approximately two and one-half centimeters long by one and one-half centimeters high, approximating the 3D pore system in the Berea sample.

One or more images of the magnified details of the slice 106 are captured by a camera 110. The images are provided to a processing system 120 for processing and transformation. The processing system 120 includes an image processing module 122. The image processing module 122 includes a computer-readable medium storing instructions executable by processors to perform operations. The image processing module 122 is configured to receive digitized images of magnified views of the slice 106, such as the images captured by the camera 110. In some embodiments, the slice 106 may include sections of rock and voids filled with epoxy prior to slicing, and the epoxy may be colored, opaque, or otherwise visually distinct from the sections. For example, the voids may be filled with an opaque epoxy to prevent the camera from imaging rock sections below the focal plane. In another example, the voids may be filled with an epoxy having a color that does not occur in the sample 102 (e.g., blue or yellow), thereby making the voids more visually distinguishable from the non-porous regions.

In some embodiments, the slice 106 or the sample 102 may be imaged using other techniques. For example, the sample 102 may be imaged using x-rays, computed tomography (CT) scans, ultrasound, or any other appropriate form of imaging that can be used to identify porous and non-porous regions within the sample 102.

The image processing module 122 processes the image into a binary matrix for transformation by a transformation module 124. The transformation module 124 includes a computer-readable medium storing instructions executable by processors to perform operations. In some implementations, the image processing module 122 can perform a threshold operation on the images, for example to convert the images from color or greyscale images to black-and-white images (e.g., arrays of binary ones and zeroes representing areas of non-porous rock and areas of porous rock). In some implementations, the image processing module 122 may perform other image processing functions, such as filtering, sharpening, softening, edge enhancement, adjustment of brightness or spectrum curves, enhancement or reduction of image resolution, masking, or combinations of these and/or any other appropriate image processing operation. For example, an epoxy having a color distinct from the sample 102 may fill the voids, and a color filter may be applied to an image of the slice 106 as part of a process of differentiating porous and non-porous regions within the slice 106. An example processed image will be discussed in the description of FIG. 2.

The binary matrix is provided to the transformation module 124. The transformation module 124 is configured to process the binary matrix to obtain statistical moments that describe the binary matrix. In some implementations, the transformation module 124 may transform the binary matrix into a statistical mean, co-variance, and/or other statistical characteristics obtained from the distribution of binary and ones and zeroes in the binary matrix. For example, the transformation module 124 may process an image of the slice 106 and determine that the slice 106 includes 55% porous area and 45% non-porous area, and that the mean pore size is 0.25 mm with a standard deviation of 0.050 mm.

The statistical moments are used by a layer generation module 126 to generate at least a first representation (e.g., first model) of a first stochastic thin section (e.g., first layer) and a second representation (e.g., second model) of a second stochastic thin section (e.g., second layer). The layer generation module 126 includes a computer-readable medium storing instructions executable by processors to perform operations. Each representation identifies a distribution of porous and non-porous sub-regions within the stochastic thin section it represents. The distribution is determined based on the statistical moments. Continuing the previous example in which the transformation module 124 may determine that the slice 106 includes 10% porous area and 90% non-porous area, and that the mean pore size is 0.010 mm with a standard deviation of 0.002 mm, in such an example, the layer generation module 126 may generate the first representation and the second representation as two different (e.g., randomized) distributions of about 10% porous and about 90% non-porous sub-regions, with about 68% (e.g., one standard deviation) of the pores ranging from 0.20 mm to 0.30 mm in size. In some implementations, multiple point statistical techniques can be used to generate the different representations or layers.

An arrangement module 128 arranges at least the first representation and the second representation such that the first stochastic layer and the second stochastic layer are arranged as adjacent layers emulative of the rock sample 102. The arrangement module 128 includes a computer-readable medium storing instructions executable by processors to perform operations. For example, the first representation and the second representation can represent generally two-dimensional slices of a three-dimensional model, and the arrangement module 128 can arrange these slices to create the three-dimensional model. Since each of the layers has a 2D distribution of pores emulating that of the slice 106, the resulting three-dimensional model can have a 3D distribution of pores emulating that of the sample 102.

In some implementations, the arrangement module 128 can arrange at least the first representation and the second representation as a 3D representation. For example, the arrangement module 128 can transform (e.g., extrude) the essentially 2D model of the first representation into a first 3D layer representation having a thickness substantially less than either its width and length, and transform (e.g., extrude) the essentially 2D model of the second representation into a second 3D layer representation having a thickness substantially less than either its width and length. The arrangement module 128 can arrange the first 3D layer representation and the second 3D layer representation as adjacent layers in a 3D model having a thickness of the two adjacent 3D layers. Additional layers based on the slice 106 can be added in a similar manner to create a 3D model of even greater combined thickness.

The system 100 also includes a 3D printer 140 or other form of 3D fabricator. In the illustrated example, the 3D printer 140 is an additive manufacturing device for the formation of a physical, 3D object, in which primarily additive processes may be used to lay down successive layers of material under computer control. In some embodiments, however, subtractive manufacturing (e.g., machining) techniques, other deposition techniques (e.g., stereolithography), erosive techniques, extrusion techniques, molding techniques, or combinations of these and/or any other appropriate manufacturing processes.

The processing system 120 provides the first representation and the second representation to the 3D printer 140 for manufacturing as a 3D fluid flow micromodel 160. The 3D printer deposits a physical 3D layer 150a based on the first representation and deposits a physical 3D layer 150b on top of the physical 3D layer 150a, based on the second representation. In some implementations, additional representations may be provided to the 3D printer for deposition as additional layers to form the 3D fluid flow micromodel 160.

In some implementations, the processing system 120 can provide the first representation and the second representation to the 3D printer 140 as the 3D model. For example, the processing system 120 can transform the 3D, which includes the first representation and the second representation, into a collection of commands for the 3D printer 140. The processing system 120 may provide the entire collection of commands to the 3D printer 140, or the processing system 120 may stream subsets of the collection to the 3D printer 140, e.g., up to the capacity of a command buffer in the 3D printer 140.

In some implementations, the processing system 120 can provide the first representation and the second representation to the 3D printer 140 separately. For example, the processing system 120 can transform the first representation into a collection of commands for the 3D printer 140, which the 3D printer 140 can deposit as the physical 3D layer 150a. The processing system 120 can then transform the second representation into a collection of commands for the 3D printer 140, which the 3D printer 140 can deposit as the physical 3D layer 150b on top of the physical 3D layer 150a. In some implementations, there may be no need to provide more than one layer's worth of commands to the 3D printer 140 at a time, since previous representations have already been formed as physical layers, and subsequent representations may not be relevant to the printing process until the current layer is complete.

Figure 2:
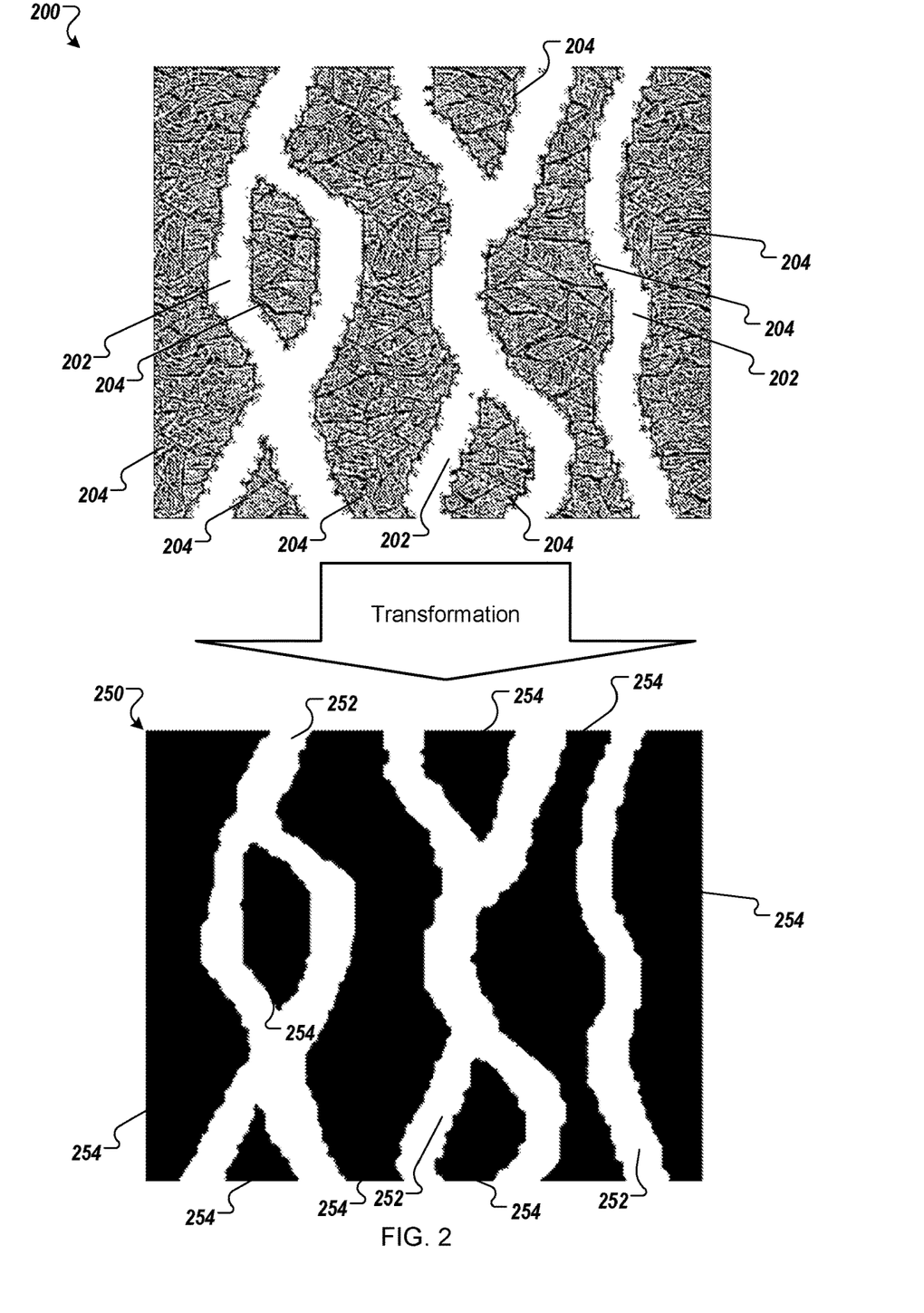
FIG. 2 is an example image of a slice of a porous media sample to which machine image processing has been applied.

FIG. 2 is an example image 200 of a slice of a porous media sample to which machine image processing has been applied. In some implementations, the image 200 may be an image of the slice 106 of FIG. 1. The image 200 shows a collection of porous regions 202 (e.g., pores) and a collection of non-porous regions 204 (e.g., rock).

The image 200 is processed, for example by the image processing module 122 and the transformation module 124, into a binary matrix 250. In the illustrated example, the binary matrix 250 is represented as a black and white image, with each binary "1" being represented by a black pixel and every binary "0" being represented by a white pixel.

Generally speaking, the image 200 is a color or greyscale image to which one or more image processing steps (e.g., thresholding, edge detection, brightness/contrast adjustments, sharpening, blurring) are applied in order to obtain a representative black and white image in which porous sub regions appear as a collection of white sub regions 252 and non-porous sub regions appear as a collection of black sub regions 254. For example, the pixels in the image 200 may be inspected to compare the brightness level the pixels to a threshold brightness level. Pixels having brightness levels equal to or greater than the threshold may be represented by a binary value of "1", and pixels having brightness levels less than the threshold may be represented by a binary value of "0".

Figure 3:
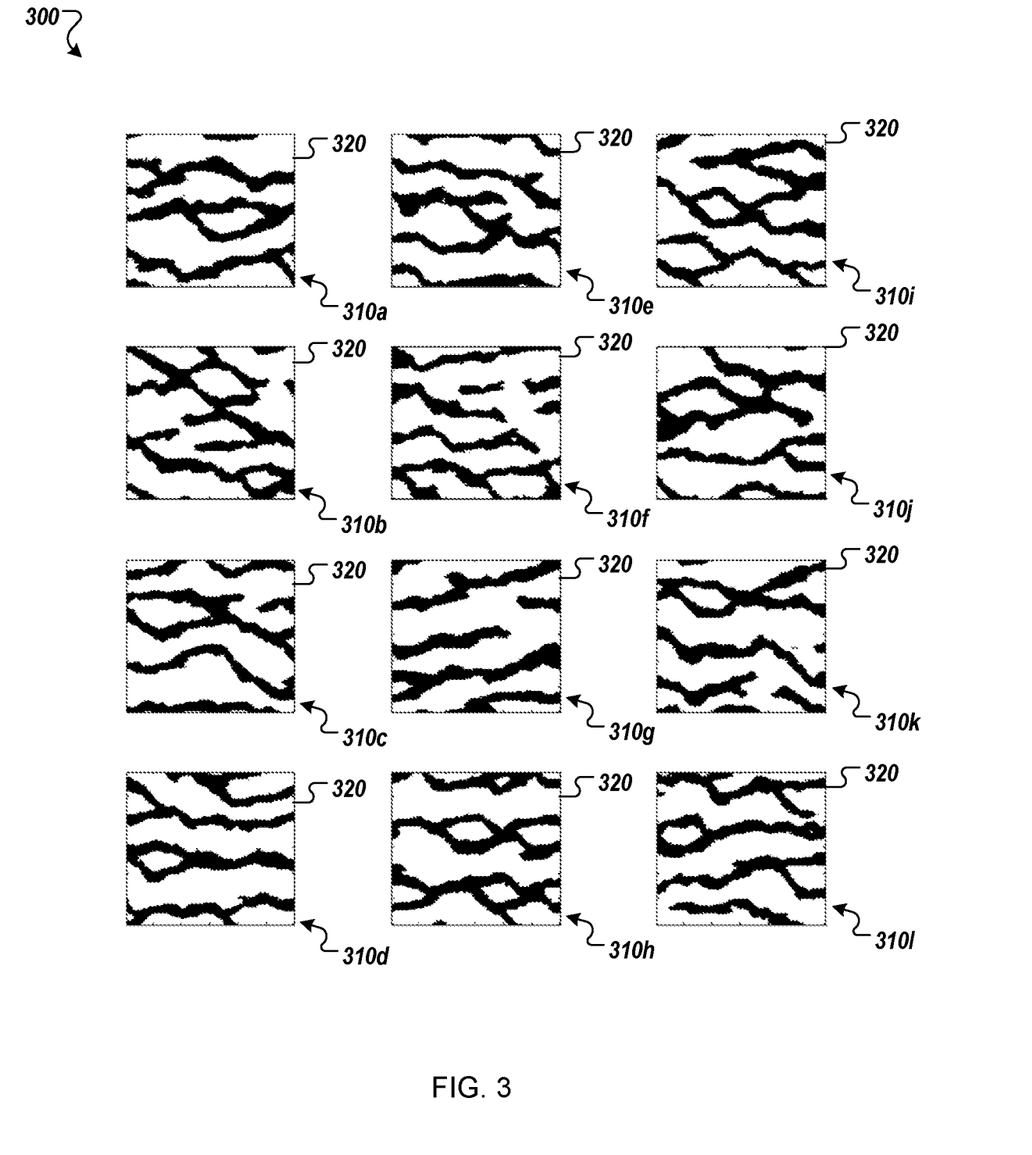
FIG. 3 shows a collection of example representations of stochastic layers emulative of a porous media sample.

FIG. 3 shows a collection 300 of example representations 310a-310l of stochastic layers that are emulative of a porous media sample. In some implementations, the representations 310a and 310b can represent the physical 3D layers 150a and 150b of FIG. 1 respectively.

The representations 310a-310l in the collection 300 are generated (e.g., by the layer generation module 126) based on a collection of statistical moments determined from an image of a sample (e.g., the image 200 of FIG. 2). For example, the image 200 may be determined to have a mean pore size of X and a co-variance of Y, and the layer generation module 126 may generate the collection 300 such that each of the representations 310a-310l has a pseudo-random distribution of pores having a mean pore size of approximately X and a co-variance of approximately Y, and such that each of the representations 310a-310l can be different from at least some of the other representations 310a-310l in the collection 300.

In some implementations, the layer generation module 126 can modify the representations 310a-310l prior to or after inclusion in the collection 300. In some implementations, the layer generation module 126 may identify one or more outer boundaries of the representations 310a-310l and close any representations of pores (e.g., convert binary ones into binary zeroes) that occur within a predetermined depth of the identified outer boundaries with a boundary layer 320. In some implementations, by closing pores that occur at or near an outer boundary, the network of pores may be prevented from allowing fluid to flow out from the outer boundary, e.g., to emulate selected geological formations, to prevent atmospheric pressures from affecting experiments, to prevent ambient air from entering the pore network.

Figure 4:
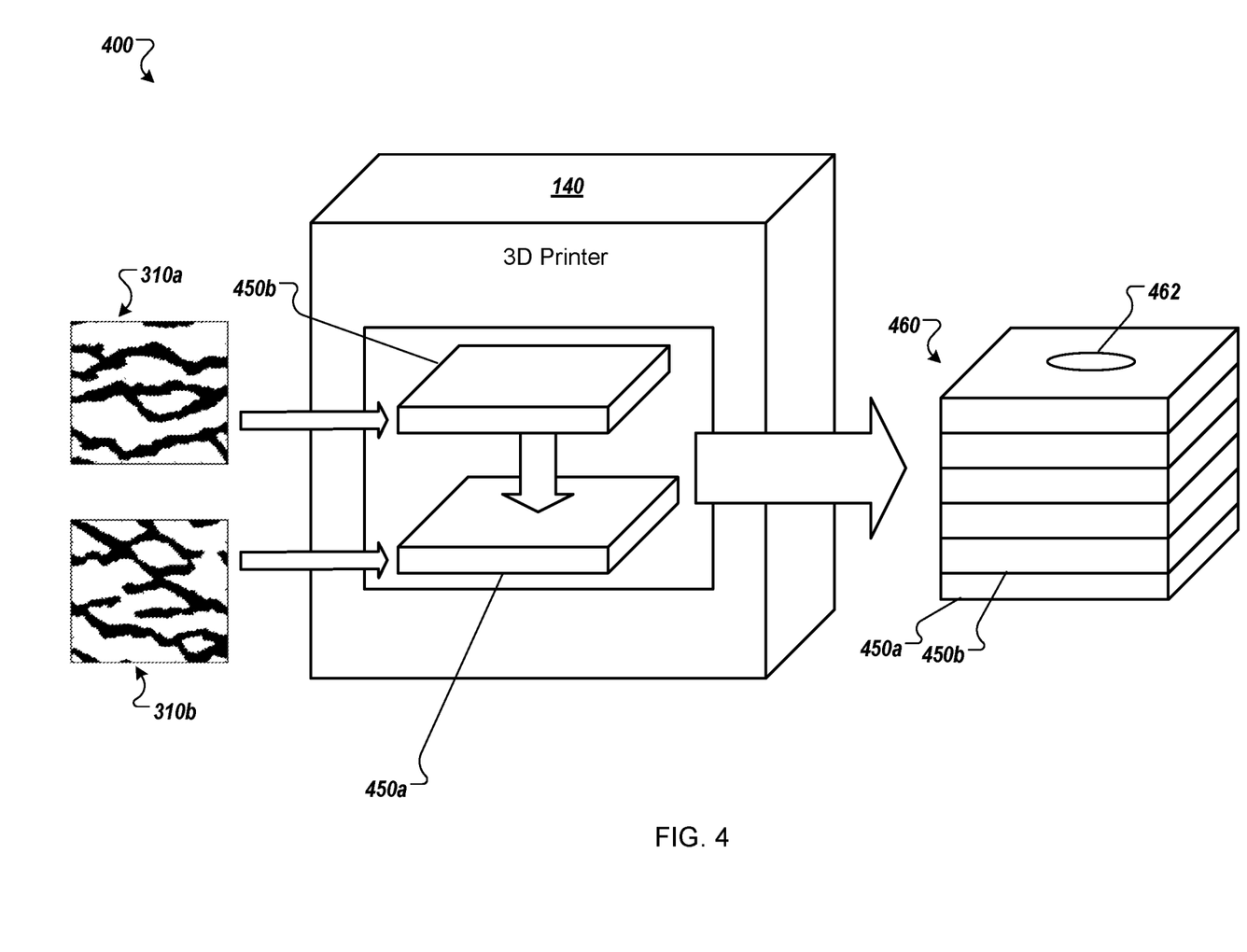
FIG. 4 is a schematic diagram of two of the example representations of stochastic layers being arranged by a 3D fabricator as adjacent layers emulative of the rock sample.

FIG. 4 is a schematic diagram 400 of two of the example representations of stochastic layers being arranged by the 3D printer 140 of FIG. 1 as adjacent layers emulative of the rock sample. In the illustrated example, the representations 310a and 310b of FIG. 3 are provided to the 3D printer 140. For example, the arrangement module 128 of FIG. 1 may provide the representations 310a, 310b as collections of commands formatted in a communications protocol that is compatible with the 3D printer 140.

The 3D printer 140 forms the representation 310a into a physical 3D layer 450a. In some embodiments, the physical 3D layer 450a can be the physical 3D layer 150a of FIG. 1. Generally speaking, wherever a binary "1" is found in the 2D binary matrix from which the representation 310a was generated, the 3D printer 140 will deposit printing filament material in a corresponding position in the physical 3D layer, and wherever a binary "0" is found in the 2D binary matrix from which the representation 310a was generated, the 3D printer 140 will leave an unfilled void. The resulting physical 3D layer 450a will have a pore network of fills and voids that are distributed according to the statistical moments determined from the sample 102

The 3D printer 140 then forms the representation 310b into the physical 3D layer 450b. In some embodiments, the physical 3D layer 450a can be the physical 3D layer 150a of FIG. 1. The physical 3D layer 450b is formed adjacent to (e.g., on top of) the physical 3D layer 450b. The physical 3D layer 450a and the adjacent physical 3D layer 450b combine to become two layers of a 3D fluid flow micromodel 460. Additional representations 310a-310l can be formed by the 3D printer 140 into additional layers of the 3D fluid flow micromodel 460. In some implementations, the 3D fluid flow micromodel 460 can be the 3D fluid flow micromodel 160.

In some implementations, the arrangement module 128 may modify the representations 310a-310l and/or a corresponding 3D representation prior to fabrication by the 3D printer 140. In some implementations, the arrangement module 128 may identify one or more sub regions of the 3D representation, such as one or more of the outer boundaries of the 3D representation, and close any representations of pores (e.g., convert binary ones into binary zeroes) that occur within the identified sub regions. For example, by closing pores that occur at or near an outer boundary, the network of pores may be prevented from allowing fluid to flow out from the outer boundary of the resulting 3D fluid flow micromodel, e.g., to emulate selected geological formations, to prevent atmospheric pressures from affecting experiments, to prevent ambient air from entering the pore network. In some implementations, pores near an outer boundary may be closed in other ways. For example, additional binary zeroes may be added beyond the edges of representations 310a-310l (e.g., to form a substantially solid z-axis barrier when the representations 310a-310l are stacked), and/or one or more additional solid (e.g., all zero) representations may be added as first and/or last representations in the collection (e.g., to form substantially solid top and bottom layers of the 3D fluid flow micromodel). In another example, a fabricated 3D fluid flow micromodel may be coated with a sealant after fabrication.

In some implementations, the arrangement module 128 may modify the representations 310a-310l and/or a corresponding 3D representation prior to fabrication by the 3D printer 140 by adding one or more fluid ports, such as a fluid port 462. For example, the fluid port 462 can be an injection port where fluid may be introduced into the 3D fluid flow model 460, or the port fluid 462 can be a production port where fluid may flow out of the 3D fluid flow model 460.

In some implementations, the arrangement module 128 may modify the representations 310a-310l and/or a corresponding 3D representation prior to fabrication by the 3D printer 140 by transforming a degree of heterogeneity of the 3D representation by applying a moving average to the distribution of the three-dimensional network of pores within the three-dimensional representation. For example, each of the individual representations 310a-310l may have their pores distributed across a substantially X-Y plane according to the statistical moments determined from the slice 106, but the distribution of pores in the Z dimension of a resulting 3D assemblage of the representations 310a-310l (e.g., as layers of the 3D assemblage) may not necessarily reflect the statistical moments of the sample 102. For example, some sub regions within the resulting 3D assemblage may be overly dense (e.g., too much non-porous material) while some sub regions may be overly sparse (e.g., too many pores) compared to the sample 102. The assembly module 128 may apply a moving average or other appropriate transformation algorithm to the distribution of binary ones and zeroes in the resulting 3D assemblage to more evenly redistribute the voids and fills within the 3D representation and the resulting fabricated 3D fluid flow micromodel.

Figure 5:
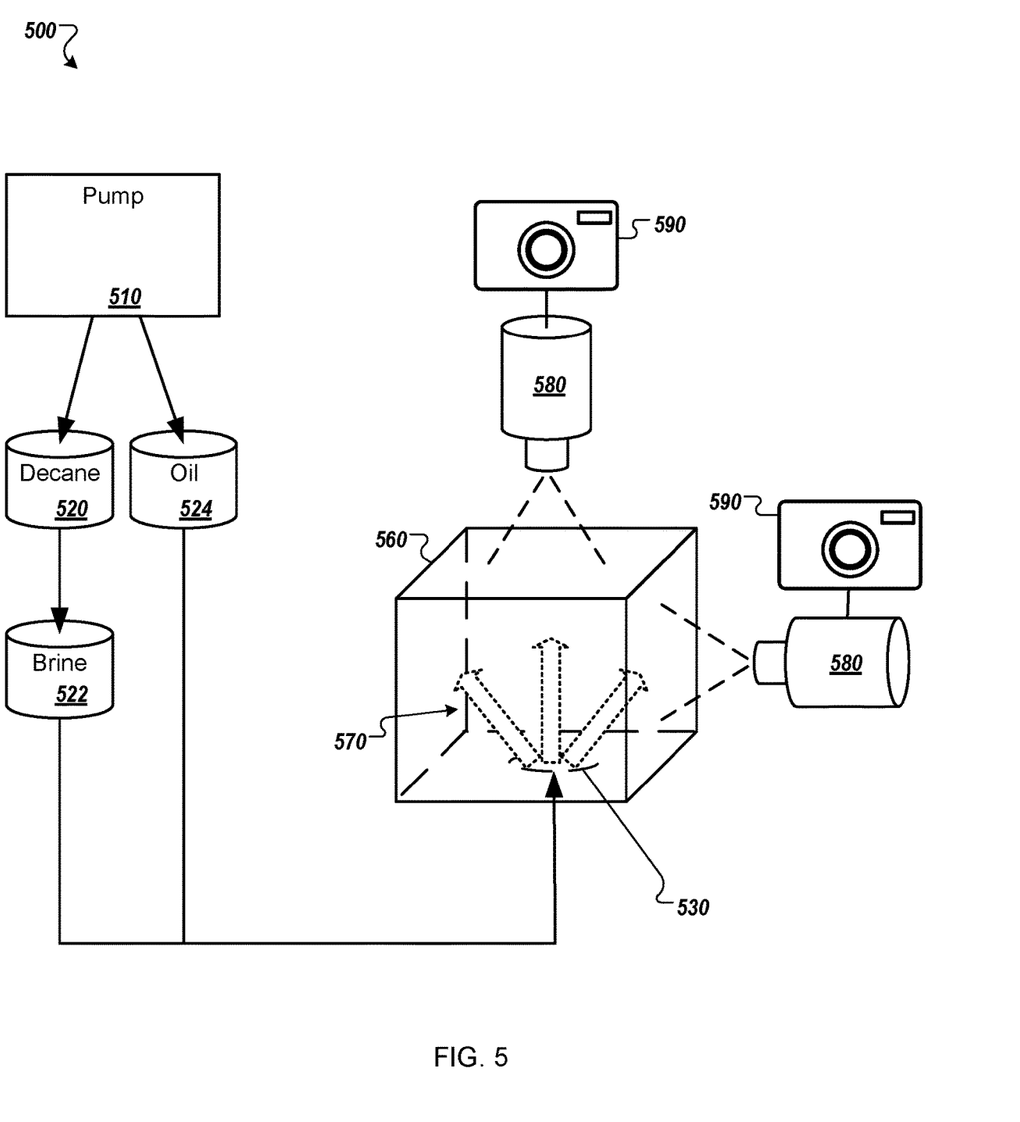
FIG. 5 is a schematic diagram of an example testing system that uses 3D fluid micromodels.

FIG. 5 is a schematic diagram of an example testing system 500 that uses 3D fluid micromodels. The system 500 includes a 3D fluid flow micromodel 560. In some embodiments, the 3D fluid flow micromodel 560 can be the 3D fluid flow micromodel 160 of FIG. 1 or the 3D fluid flow micromodel 460 of FIG. 4. A pump 510 urges the flow of fluids from a decane reservoir 520, a brine reservoir 522, an oil reservoir 524, and/or any other appropriate fluid though an inlet port 530 in the 3D fluid flow micromodel 560.

The pump 510 urges the fluids to flow into a pore network (not shown) of the 3D fluid flow micromodel 560, as represented by arrows 570. The pore network is emulative of a porous material, such as the sample 102. The 3D fluid flow micromodel 560 is formed of a substantially transparent material. As the fluids flow through the pore network formed in the transparent material, the movement of the fluids is observable from outside of the 3D fluid flow micromodel 560.

A collection of microscopes 580 and cameras 590 are configured to capture one or more views of the 3D fluid flow micromodel 560 and one or more views of the fluids as they flow through the pore network of the 3D fluid flow micromodel 560. In some embodiments, the microscopes 580 and cameras 590 may be configured to capture a collection of images from multiple angles as substantially the same time. In some embodiments, multiple images taken of the 3D fluid flow micromodel 560 from multiple angles may be processed to create a 3D fluid distribution model (e.g., a computer model or simulation that may be stored for later inspection). In some embodiments, multiple 3D fluid distribution models may be arranged (e.g., sequenced) to create a 3D fluid flow model (e.g., a dynamic computer model or simulation of the fluid flow that may be stored for later inspection).

In some embodiments, since the 3D fluid flow micromodel 560 includes a pore network that is emulative of a porous material, such as the sample 102, the flow of fluids through the 3D fluid flow micromodel 560 can be emulative of the flow of fluids through the sampled porous material. In some embodiments, since the 3D fluid flow micromodel 560 can be formed of substantially transparent material, the flow of fluids through the pore network can be observed (e.g., unlike the sampled porous material, which is likely to be opaque). As such, an approximation of a 3D flow of fluids through the sampled porous (opaque) material can be observed.

Figure 6:
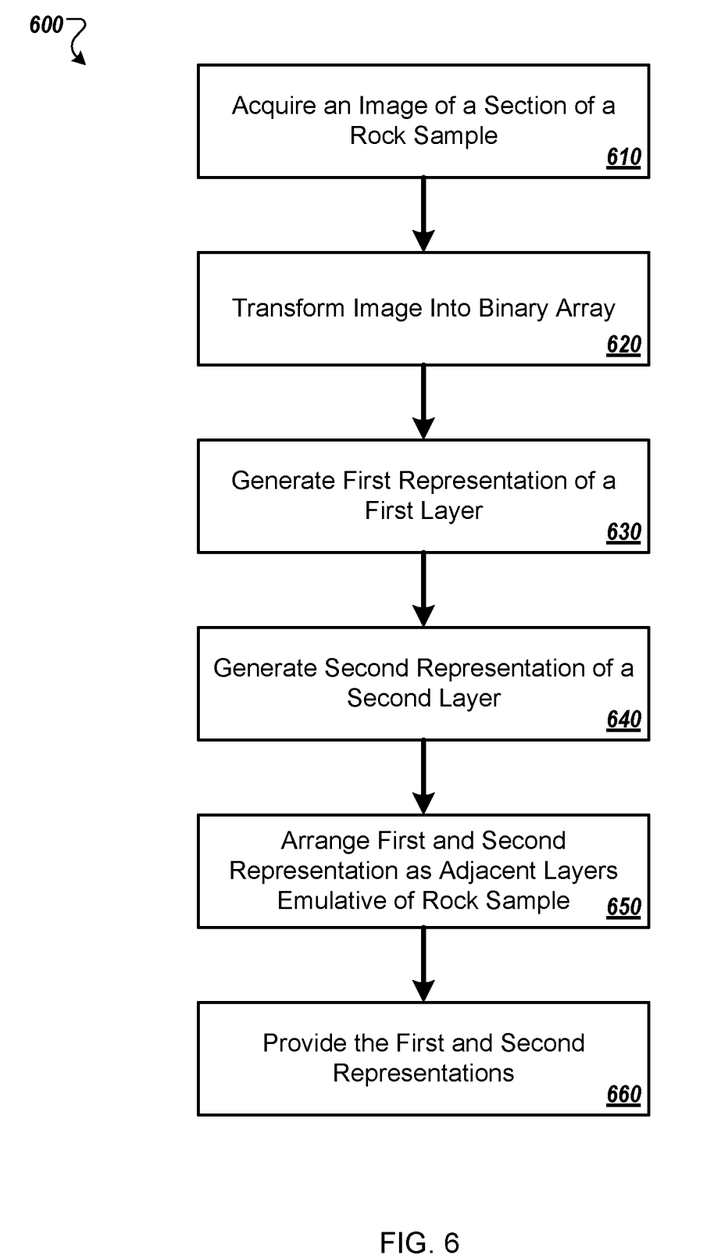
FIG. 6 is a flow diagram of an example process for creating a 3D fluid micromodel emulative of a porous media sample.

FIG. 6 is a flow diagram of an example process 600 for creating a 3D fluid micromodel emulative of a porous media sample. In some implementations, the process 600 may be performed by the system 100 of FIG. 1.

At 610 an image of a section of a rock sample having a network of pores is acquired. For example, the camera 110 can image the slice 106 of the sample 102. The image can then be provided to the processing system 120. In some implementations, the image may be processed by the image processing module 122 to enhance or otherwise prepare the image for further processing.

At 620 the image is transformed into a binary matrix. For example, transformation module 124 can compare the brightness values or other properties of the pixels of the image 200 of FIG. 2 to a predetermined threshold value to produce the binary matrix 250. Pixels having values equal to or greater than the threshold can each be represented by binary "1's" at locations within a binary matrix (e.g., array) corresponding to the locations of the pixels in the acquired image. Pixels having values less than the threshold can each be represented by a binary "0's" at locations within the binary matrix corresponding to the locations of the pixels in the acquired image. In some implementations, the binary matrix may be visualized as a black and white 2D image in which porous sub regions appear as the collection of white sub regions 252 and non-porous sub regions appear as the collection of black sub regions 254.

At 630, a first representation of a first stochastic layer is generated based on a set of one or more statistical moments of the binary matrix and emulative of the rock sample. For example, transformation module 124 may process the distribution of binary ones and zeroes within the binary matrix 250 to determine a statistical mean, covariance, or combinations of these and/or any other appropriate mathematical (e.g., statistical) description of the distribution of porous and non-porous sub-regions within the sample 102. The layer generation module 126 can then create a first representation, such as the representation 310a of FIG. 3, with a pseudo-random distribution of fills and voids that is based on the set of statistical moments, thereby emulating the distribution of fills and voids in the slice 106.

In some implementations, the set of one or more statistical moments can be determined by applying multiple-point statistical methods to an image of the slice 106 to produce a stochastic realization based on the original thin section image. For example, a single normal equation simulation (SNESIM) and/or a filter-based process (FILTERSIM) can be used. In some implementations, the SNESIM approach can be used to read the conditional distributions from a training image. In some implementations, the FILTERSIM process can accept approximate replicates of a conditioned data event and classify local patterns present in the training image into a predetermined number of bins of similar-looking patterns. In some implementations, the FILTERSIM process can perform this classification using linear filters that are applied to the pixel data set that defines the pattern. In some examples, the FILTERSIM process can be used when a large number of categorical variables (e.g., >4) are to be simulated jointly, and the SNESIM process can used when a predetermined small number of categories are present given the availability of a large and varied training image.

At 640, a second representation of a second stochastic layer is generated based on the set and emulative of the rock sample, the second representation being different from the first representation. For example, the layer generation module 126 can then create a second representation, such as the representation 310b, with a pseudorandom distribution of fills and voids that is based on the set of statistical moments, thereby emulating the distribution of fills and voids in the slice 106 yet differing from the distribution of the representation 310a.

At 650, the first representation and the second representation are arranged such that the first stochastic layer and the second stochastic layer are arranged as adjacent layers of a three-dimensional model emulative of the rock sample. For example, the arrangement module 128 can arrange the representations 310a and 310b, each being a 2D binary array, as two adjacent layers in a 3D binary array that can be used as a 3D representation of the 3D fluid flow micromodel 160.

At 660, the first representation and the second representation are provided as adjacent layers of the three-dimensional model emulative of the rock sample. For example, the arrangement module 128 may provide the first representation and the second representation, either separately or jointly as electronic data (e.g., a computer-generated three-dimensional model) that may be stored, retrieved, and/or edited. In another example, the 3D printer 140 may provide the first representation and the second representation adjacently as the physical 3D layers 150a and 150b of the 3D fluid flow micromodel 160.

In some implementations, a three-dimensional fluid micromodel emulative of the rock sample can be formed, and the forming can include forming a first micromodel layer comprising a network of pores based on the first representation, and forming a second micromodel layer comprising a network of pores based on the second representation adjacent the first micromodel layer. In some implementations, a 3D printer or other 3D fabricator can be used to form the three-dimensional fluid micromodel emulative of the rock sample. For example, the 3D printer 160 can be used to form the physical 3D layer 450a and the physical 3D layer 450b as two layers of the 3D fluid flow micromodel 460.

In some implementations, forming the first micromodel layer can include providing the first representation as a first collection of commands to the 3D printer, and printing, by the 3D printer, the first micromodel layer as a first printed layer in a three-dimensional printed model. In some implementations, forming at least the second micromodel layer can include providing the second representation as a second collection of commands to the 3D printer, and printing, by the 3D printer, the second micromodel layer as a second printed layer in the three-dimensional printed model. For example, the arrangement module 128 may convert the representation 310a to a collection of commands that are provided to the 3D printer 160, in which the commands direct the 3D printer 160 to fabricate the physical 3D layer 450a. The arrangement module 128 may then convert the representation 310b to a collection of commands that are provided to the 3D printer 160, in which the commands direct the 3D printer 160 to fabricate the physical 3D layer 450b.

In some implementations, the first representation and the second representation can be arranged into a three-dimensional representation based on the set of statistical moments, in which the three-dimensional representation has a three-dimensional network of pores emulative of the rock sample. For example, the arrangement module 128 may arrange two or more of the representations 310a-310l, each of the representations 310a-310l being a 2D binary matrix, as adjacent layers of a 3D binary matrix. The resulting 3D binary matrix can be used as a virtual 3D model that is emulative of the sample 102.

In some implementations, at least one boundary on or within the three-dimensional representation can be identified, and pores can be removed from the boundary. For example, the outer boundaries of a 3D binary matrix emulative of the sample 102 can be identified, and every binary location within five locations of an outer boundary can each be assigned a value of "0", representative of non-porous locations, to substantially seal the outer surface of the virtual 3D model and cause a resulting physical 3D model to have an outer surface that is substantially non-porous.

In some implementations, at least one of an injection port or a production port can be included in the 3D representation. For example, the arrangement module 128 can modify the representations 310*a*-310*l* and/or add additional representations to include a fluid injection port such as the fluid port 530 where fluid can be introduced into the 3D fluid flow micromodel 560 or a production port such as the fluid port 462 where fluid can flow out of the 3D fluid flow micromodel 460.

In some implementations, a degree of heterogeneity of the three-dimensional representation can be transformed by applying a moving average to the distribution of the three-dimensional network of pores within the three-dimensional representation. For example, the arrangement module 128 can process the 3D binary matrix, which can be a Z-axis arrangement of the 2D (e.g., XY) representations 310*a*-310*l*, to apply a moving average to the Z axis distribution of binary ones and zeroes (e.g., representing voids and fills) within the 3D binary matrix. The arrangement module 128 can redistribute the Z axis distribution of binary ones and zeroes based on the moving average.

Figure 7:
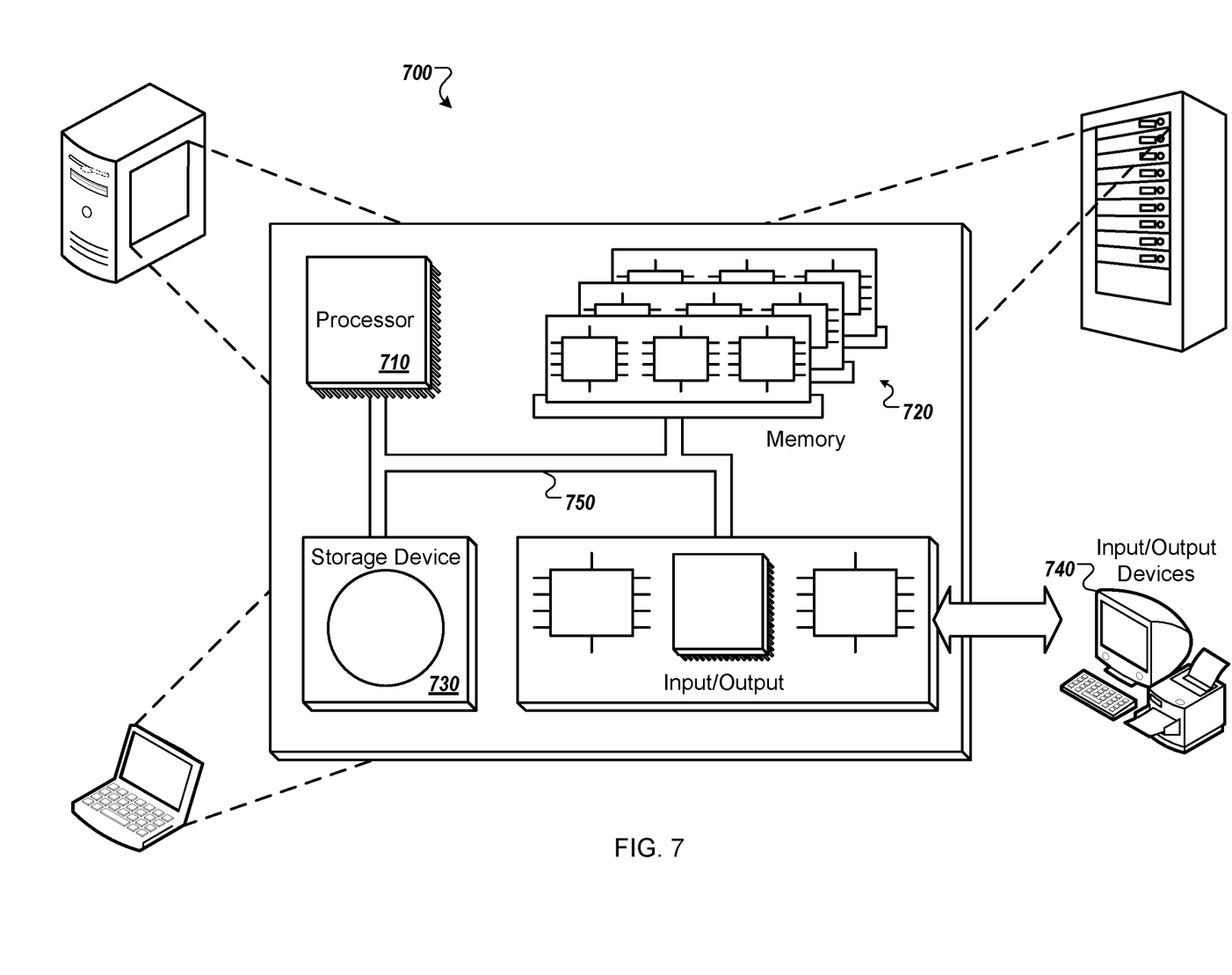
FIG. 7 is a schematic diagram of an example of a generic computer system that can be used to perform the processes described in this document.

FIG. 7 is a schematic diagram of an example of a generic computer system 700. The system 700 can be used for the operations described in association with the method 600 according to one implementation. For example, the system 700 may be included in either or all of the processing system 120 of FIG. 1.

The system 700 includes a processor 710, a memory 720, a storage device 730, and an input/output device 740. Each of the components 710, 720, 730, and 740 are interconnected using a system bus 750. The processor 710 is capable of processing instructions for execution within the system 700. In one implementation, the processor 710 is a single-threaded processor. In another implementation, the processor 710 is a multi-threaded processor. The processor 710 is capable of processing instructions stored in the memory 720 or on the storage device 730 to display graphical information for a user interface on the input/output device 740.

The memory 720 stores information within the system 700. In one implementation, the memory 720 is a computer-readable medium. In one implementation, the memory 720 is a volatile memory unit. In another implementation, the memory 720 is a non-volatile memory unit.

The storage device 730 is capable of providing mass storage for the system 700. In one implementation, the storage device 730 is a computer-readable medium. In various different implementations, the storage device 730 may be a floppy disk device, a hard disk device, an optical disk device, or a tape device.

The input/output device 740 provides input/output operations for the system 700. In one implementation, the input/output device 740 includes a keyboard and/or pointing device. In another implementation, the input/output device 740 includes a display unit for displaying graphical user interfaces. In another implementation, the input/output device 740 can be the 3D printer 160. In another implementation, the input/output device 740 can be one or more of the cameras 108 of FIG. 1 or 590 of FIG. 5.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

Although a few implementations have been described in detail above, other modifications are possible. For example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A non-transitory computer-readable medium storing instructions executable by a processing device to perform operations comprising:
    acquiring, by a computer device, an image of a section of a rock sample having a network of pores;
    transforming, by the computer device, the image into a binary matrix;
    determining, by the computer device, a set of one or more statistical characteristics of the binary matrix;
    generating, by the computer device, a first representation of a first stochastic simulated rock layer emulative of the rock sample and having a first pseudorandom distribution of porous regions and non-porous regions that is based on the determined set of one or more statistical characteristics of the binary matrix;
    generating, by the computer device, a second representation of a second simulated rock layer emulative of the rock sample and having a second pseudorandom distribution of porous regions and non-porous regions that is based on the determined set of one or more statistical characteristics of the binary matrix, the second representation being different from the first representation;
    arranging, by the computer device, the first representation and the second representation such that the first simulated rock layer and the second simulated rock layer are arranged as adjacent layers of a three-dimensional model emulative of the rock sample; and
    providing, by the computer device, the first representation and the second representation as adjacent layers of the three-dimensional model emulative of the rock sample.

2. The non-transitory computer-readable medium of claim 1, wherein arranging the first representation and the second representation further comprises:
    forming, under control of the computer device, the three-dimensional model as a physical three-dimensional fluid micromodel emulative of the rock sample, the forming comprising:
        forming a first physical micromodel layer comprising a network of pores based on the first representation; and
        forming a second physical micromodel layer comprising a network of pores based on the second representation adjacent the first physical micromodel layer.

3. The non-transitory computer-readable medium of claim 2, wherein forming the three-dimensional model as the physical three-dimensional fluid micromodel emulative of the rock sample comprises:
    providing, by the computer device, the first representation as a first collection of commands to a three-dimensional printer; and
    printing, by the three dimensional printer, the first physical micromodel layer as a first printed layer in a physical three-dimensional printed model; and
    forming at least the second physical micromodel layer further comprises:
        providing, by the computer device, the second representation as a second collection of commands to the three-dimensional printer; and
        printing, by the three dimensional printer, the second physical micromodel layer as a second printed layer in the physical three-dimensional printed model.

4. The non-transitory computer-readable medium of claim 1, wherein arranging the first representation and the second representation further comprises:
    arranging, by the computer device, the first representation and the second representation into a computer-generated three-dimensional representation based on the set, the computer-generated three-dimensional representation comprising a three-dimensional network of pores emulative of the rock sample; and
    transforming, by the computer device, a degree of heterogeneity of the computer-generated three-dimensional representation by applying a moving average to the distribution of the three-dimensional network of pores within the computer-generated three-dimensional representation.

5. The non-transitory computer-readable medium of claim 4, the operations further comprising:
    identifying, by the computer device, at least one outer boundary of the computer-generated three-dimensional representation; and
    removing pores from the outer boundary.

6. The non-transitory computer-readable medium of claim 1, the operations further comprising determining, by the computer device, the determined set of one or more statistical characteristics of the binary matrix, wherein the set comprises one or more of a statistical mean and a statistical covariance.

7. A system comprising:
    a three-dimensional (3D) fabricator;
    an image processing module configured to acquire an image of a section of a rock sample having a network of pores;
    a transformation module configured to transform the image into a binary matrix and determine a set of one or more statistical characteristics of the binary matrix, the set comprising one or more of a statistical mean and a statistical covariance;
    a layer generation module configured to:
        generate a first representation of a first simulated rock layer emulative of the rock sample and having a first pseudorandom distribution of porous regions and non-porous regions that is based on the set of one or more statistical characteristics of the binary matrix; and
        generate a second representation of a second simulated rock layer emulative of the rock sample and having a second pseudorandom distribution of porous regions and non-porous regions that is based on the set of one or more statistical characteristics of the binary matrix, the second representation being different from the first representation; and
    an arrangement module configured to arrange the first representation and the second representation such that the first simulated rock layer and the second simulated rock layer are arranged as adjacent layers of a three-dimensional model emulative of the rock sample, and provide the first representation and the second representation to the 3D fabricator for fabrication as a physical three-dimensional fluid micromodel emulative of the rock sample, the physical three-dimensional fluid micromodel comprising a first physical micromodel layer comprising a first network of pores based on the first representation, and a second physical micromodel layer comprising a second network of pores based on the second representation, adjacent the first physical micromodel layer.

8. The system of claim 7, wherein:

the arrangement module is a three-dimensional printer;

the first representation is presented as a first collection of commands to the three-dimensional printer for printing as a first printed layer in the physical three-dimensional fluid micromodel; and the second representation is presented as a second collection of commands to the three-dimensional printer for printing as a second printed layer in the physical three-dimensional fluid micromodel.

9. The system of claim 7, wherein the arrangement module is further configured to:

arrange the first representation and the second representation into a computer-generated three-dimensional representation based on the set, the computer-generated three-dimensional representation comprising a three-dimensional network of pores emulative of the rock sample; and identify at least one outer boundary of the three-dimensional computer-generated representation, and remove pores from the outer boundary.

10. The system of claim 7, wherein the arrangement module is further configured to:

arrange the first representation and the second representation into a three-dimensional representation based on the set, the three-dimensional representation comprising a three-dimensional network of pores emulative of the rock sample; and transform a degree of heterogeneity of the three-dimensional representation by applying a moving average to the distribution of the three-dimensional network of pores within the three-dimensional representation.

\* \* \* \* \*

UNITED STATES PATENT AND TRADEMARK OFFICE
CERTIFICATE OF CORRECTION

| | |
|---|---|
| PATENT NO. | : 11,590,708 B2 |
| APPLICATION NO. | : 16/014525 |
| DATED | : February 28, 2023 |
| INVENTOR(S) | : Ali Alkhatib, Amar Alshehri and Ming Han |

It is certified that error appears in the above-identified patent and that said Letters Patent is hereby corrected as shown below:

In the Claims

In Column 15, Line 27, Claim 1, please replace "first stochastic" with -- first --.

Signed and Sealed this
Twenty-seventh Day of August, 2024

Katherine Kelly Vidal
*Director of the United States Patent and Trademark Office*